(12) United States Patent
Schmidt

(10) Patent No.: US 12,415,067 B2
(45) Date of Patent: Sep. 16, 2025

(54) SPINAL CORD STIMULATOR TUOHY NEEDLE CONNECTOR AND METHODS OF USE

(71) Applicant: Keith Schmidt, Lisle, IL (US)

(72) Inventor: Keith Schmidt, Lisle, IL (US)

( * ) Notice: Subject to any disclaimer, the term of this patent is extended or adjusted under 35 U.S.C. 154(b) by 479 days.

(21) Appl. No.: 17/944,848

(22) Filed: Sep. 14, 2022

(65) Prior Publication Data

US 2024/0082570 A1    Mar. 14, 2024

(51) Int. Cl.
*A61N 1/05* (2006.01)

(52) U.S. Cl.
CPC ................................ *A61N 1/0551* (2013.01)

(58) Field of Classification Search
CPC . A61N 1/0551; A61N 1/0502; A61N 1/36017
See application file for complete search history.

(56) References Cited

U.S. PATENT DOCUMENTS

| | | | |
|---|---|---|---|
| 2011/0230846 A1* | 9/2011 | Wen | A61B 17/3401 604/272 |
| 2014/0039586 A1* | 2/2014 | Barker | A61B 17/3468 607/116 |

* cited by examiner

*Primary Examiner* — Erin McGrath
(74) *Attorney, Agent, or Firm* — J. Peter Paredes; Amin Wasserman Gurnani LLP

(57) ABSTRACT

Provided herein are systems, methods and apparatuses for a Spinal cord stimulator touhy needle connector.

5 Claims, 2 Drawing Sheets

SPINAL CORD STIMULATOR TUOHY NEEDLE CONNECTOR AND METHODS OF USE

BACKGROUND

The invention generally relates to needle connectors and spinal cord needle connectors for spinal cord stimulation.

Dorsal column stimulation is a minimally invasive treatment for intractable pain in the back and extremities. As a pain management technique, it interferes with the transmission of pain signals from the nerves to the brain, and can significantly reduce pain and improve the ability to participate in daily activities. Dorsal column stimulation is a reversible neuromodulation technique. In current dorsal column spinal cord stimulation, two separate needles are placed in a bilaterally paramedian approach to enter the epidural space. Historically each needle is placed separately making the overall process of the trial procedure to be around 30 to 60 minutes.

The present invention attempts to solve these problems as well as others.

SUMMARY OF THE INVENTION

Provided herein are systems, methods and apparatuses for a Spinal cord stimulator Tuohy needle connector.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

BRIEF DESCRIPTION OF THE DRAWINGS

In the accompanying figures, like elements are identified by like reference numerals among the several preferred embodiments of the present invention.

DETAILED DESCRIPTION OF THE INVENTION

Figure 1:
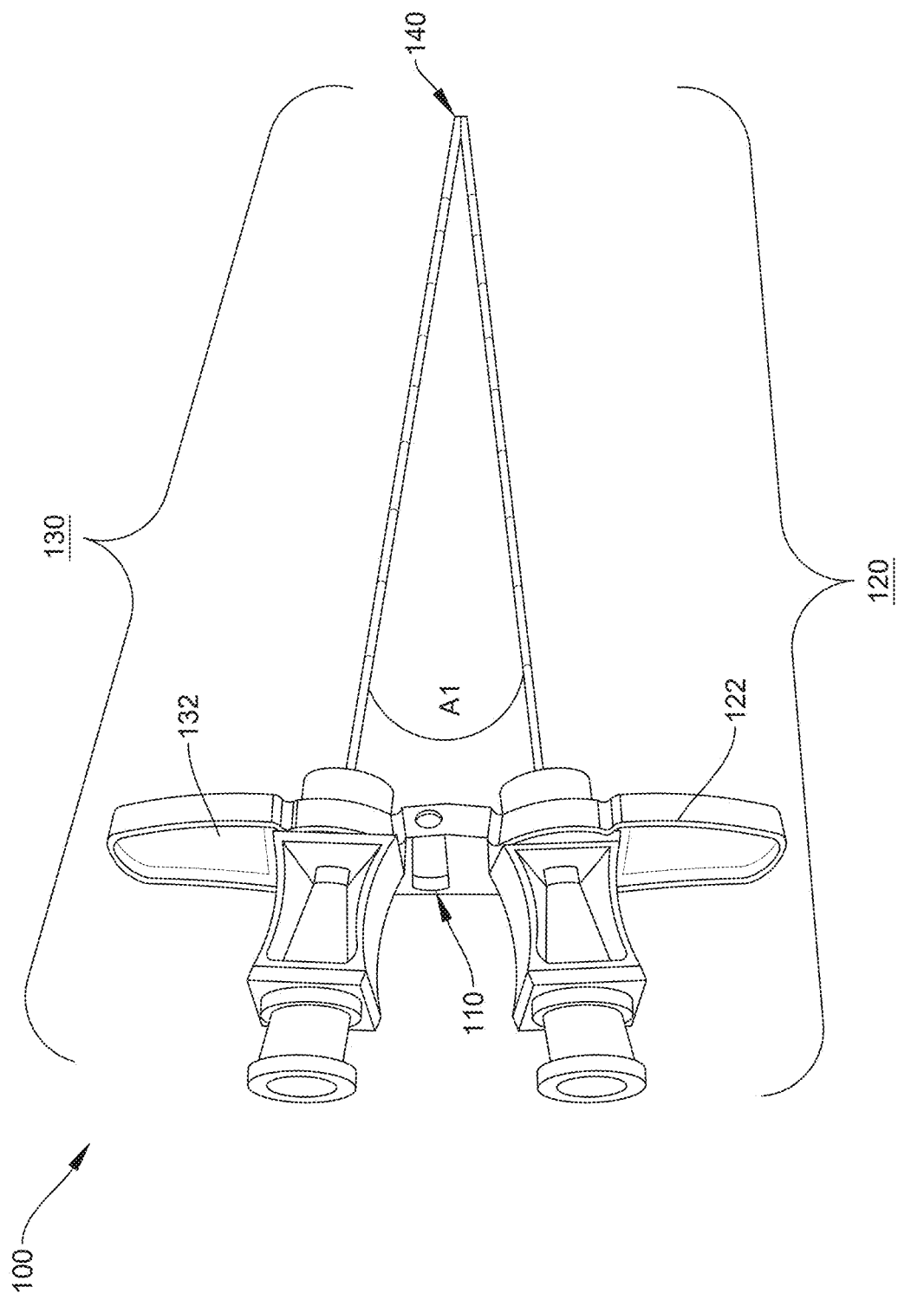
FIG. 1 is a perspective view of the Spinal cord stimulator Tuohy needle connector, according to one embodiment.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Generally speaking, the Spinal cord stimulator Tuohy needle connector increases the efficiency of spinal cord stimulator (SCS) Tuohy needle placement into the epidural space. This Spinal cord stimulator Tuohy needle connector is a monolithic bridge between the two needles, such that both needles can be placed simultaneously to enter the epidural space. In one embodiment, the Spinal cord stimulator Tuohy Tuohy needle connector decreases the overall procedure time.

The Spinal cord stimulator Tuohy needle connector comprises the two needles as to increase procedure efficiency time between about 5 about 30 minutes, decreases procedural pain for the patient, and comprises less bilateral epidural lead passes to decrease on tracks created in the epidural space.

The Spinal cord stimulator Tuohy needle connector could be made of plastic or titanium, or any biomaterial. The Spinal cord stimulator Tuohy needle connector can be shaped small or large but the Spinal cord stimulator Tuohy needle connector binds the two Tuohy needles to comprises a single lead pass in the epidural space.

Figure 2:
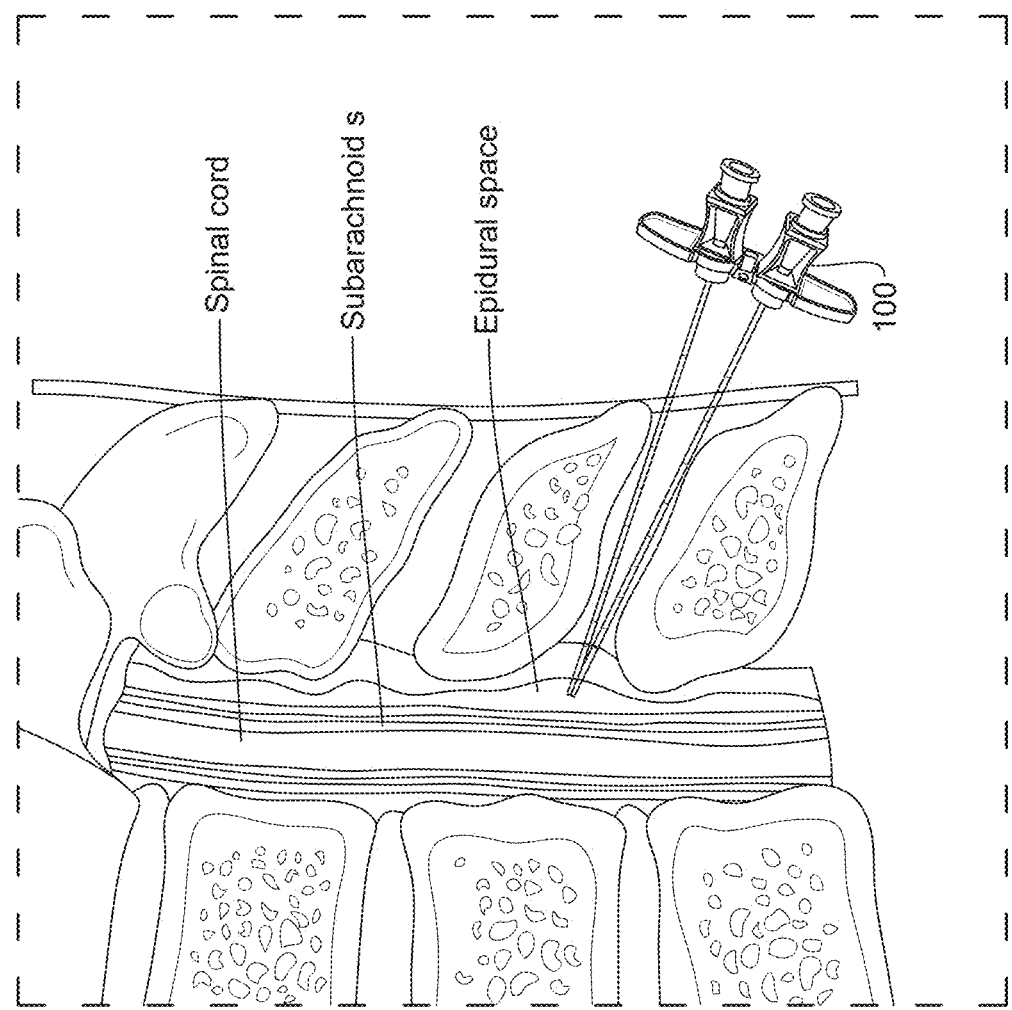
FIG. 2 is a side view of the Spinal cord stimulator Tuohy needle connector disposed into the spinal cord and the epidural space.

Spinal cord stimulator Tuohy Tuohy needle connector bridges the needles together so the needles are connected to enter the same interlaminar opening, as shown in FIG. 2. The Spinal cord stimulator Tuohy needle connector comprises the leads unsnared together, and the leads enter the same opening and be thread separately.

The Spinal cord stimulator Tuohy needle connector comprises bridge connector for the Tuohy needle. In one embodiment, Spinal cord stimulator Tuohy needle connector comprises a larger Tuohy needle intended for only the epidural space.

As shown in FIG. 1, the Spinal cord stimulator Tuohy needle connector 100 comprises a bridge connector 110 operably coupling a first Electrode Spinal Cord needle 120 and a second Electrode Spinal Cord needle 130. The bridge connector 110 operably couples the first Electrode Spinal Cord needle 120 and the second Electrode Spinal Cord needle 130 to provide an angle A1 to allow the distal ends of the first Electrode Spinal Cord needle 120 and the second Electrode Spinal Cord needle 130 to abut and form a single lead pass 140. The single lead pass 140 is between about 3 mm and about 12 mm. The first Electrode Spinal Cord needle 120 and the second Electrode Spinal Cord needle 130 operably coupled with a first electrode and a second electrode, which are both operably coupled to a battery device by way of wires. The spinal cord stimulator lead or the electrodes are fed through the first Electrode Spinal Cord needle 120 and the second Electrode Spinal Cord needle 130 by way of a lumen traversing the first Electrode Spinal Cord needle 120 and the second Electrode Spinal Cord needle 130. In one embodiment, Angle A1 between the first Electrode Spinal Cord needle 120 and the second Electrode Spinal Cord needle 130 may be between about 20 degrees and about 75 degrees; alternatively, between about 10 degrees and about 80 degrees.

In one embodiment, the first Electrode Spinal Cord needle 120 comprises a first proximal T-wing hub 122 and the second Electrode Spinal Cord needle 130 comprises a second proximal T-wing hub 132. The first proximal T-wing hub 122 and the second proximal T-wing hub 132 operably couple with the bridge connector 110 that allows the first Electrode Spinal Cord needle 120 and the second Electrode Spinal Cord needle 130 to move bilaterally or up/down by way of groove coupling between the first T-wing hub 122 and the second T-wing hub 132. In alternative embodiments, the bridge connector 110 comprises a latch point, pivot point, tongue and groove coupling, clip point, a button coupling, a magnetic coupling, or alternative connection that allows the first Electrode Spinal Cord needle 120 and the second Electrode Spinal Cord needle 130 to move bilaterally or up/down.

A method for Spinal cord stimulation is disclosed and comprises: providing a spinal cord stimulator Tuohy needle connector including a bridge connector; operably coupling a first Electrode Spinal Cord needle and a second Electrode Spinal Cord needle with the bridge connector to provide an angle $\mu l$ to allow the distal ends of the first Electrode Spinal Cord needle and the second Electrode Spinal Cord needle to abut and form a single lead pass. The method further comprises operably coupling the first Electrode Spinal Cord needle and the second Electrode Spinal Cord needle with a first electrode and a second electrode; and operably coupling the first electrode and the second electrode to a battery device by way of wires. The spinal cord stimulator lead (electrodes) which is fed through the first Electrode Spinal Cord needle 120 and the second Electrode Spinal Cord needle 130. In one embodiment, Angle $\mu l$ may be between about 20 degrees and about 75 degrees.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A spinal cord stimulator Tuohy needle connector comprising: a bridge connector operably coupling a first electrode spinal cord needle and a second electrode spinal cord needle;

the bridge connector operably couples the first electrode spinal cord needle and the second electrode spinal cord needle to provide an angle $\mu l$ to allow the distal ends of the first electrode spinal cord needle and the second electrode spinal cord needle to abut and form a single lead pass;

wherein the single lead pass is between about 3 mm and about 12 mm;

wherein a spinal cord stimulator lead is fed through the first electrode spinal cord needle and the second electrode spinal cord needle;

wherein the Angle $\mu l$ between the first electrode spinal cord needle and the second electrode spinal cord needle is between about 10 degrees and about 80 degrees;

a first proximal T-wing hub and the second electrode spinal cord needle comprises a second proximal T-wing hub, wherein the first proximal T-wing hub and the second proximal T-wing hub operably couple with the bridge connector to allow the first electrode spinal cord needle and the second electrode spinal cord needle to move bilaterally or up/down by way of a groove coupling between the first T-wing hub and the second T-wing hub.

2. The spinal cord stimulator Tuohy needle connector of claim 1, wherein the bridge connector comprises a latch point, pivot point, tongue and groove coupling, clip point, a button coupling, a magnetic coupling, or alternative connection that allows the first electrode spinal cord needle and the second electrode spinal cord needle to move bilaterally or up/down.

3. A method for spinal cord stimulation comprising: providing a spinal cord stimulator Tuohy needle connector of claim 1 including the bridge connector; operably coupling the first electrode spinal cord needle and the second electrode spinal cord needle with the bridge connector to provide the angle µl to allow the distal ends of the first electrode spinal cord needle and the second electrode spinal cord needle to abut and form the single lead pass.

4. The method of claim 3, further comprising operably coupling the first electrode spinal cord needle and the second electrode spinal cord needle with a first electrode and a second electrode.

5. The method of claim 4, further comprising feeding the spinal cord stimulator lead through the first electrode spinal cord needle and the second electrode spinal cord needle.

\* \* \* \* \*